United States Patent
Pfaff et al.

[11] Patent Number: 5,725,589
[45] Date of Patent: Mar. 10, 1998

[54] TAPERED HIP-JOINT SOCKET WITHOUT TAPER LOCK

[75] Inventors: Hans-Georg Pfaff, Ostfildern; Ernst Hoch, Notzingen; Harmut Kälberer, Deizisau, all of Germany

[73] Assignee: Cera GmbH, Innovatives-Keramik-Engineering, Plochingen, Germany

[21] Appl. No.: 634,113

[22] Filed: Apr. 17, 1996

Related U.S. Application Data

[63] Continuation of Ser. No. 344,348, Nov. 22, 1994, abandoned.

[30] Foreign Application Priority Data

Nov. 26, 1993 [DE] Germany ............ 43 40 304.2
Jan. 29, 1994 [DE] Germany ............ 44 02 675.7

[51] Int. Cl.[6] ..................................... A61F 2/32
[52] U.S. Cl. ............................................ 623/22
[58] Field of Search ................... 623/16, 18, 19, 623/22, 23

[56] References Cited

U.S. PATENT DOCUMENTS

| | | | |
|---|---|---|---|
| Re. 31,865 | 4/1985 | Roux | 623/22 |
| 4,180,873 | 1/1980 | Fixel | 623/22 |
| 4,566,188 | 1/1986 | Lewis et al. | 623/22 |
| 4,908,033 | 3/1990 | Frey et al. | 623/22 |
| 5,092,897 | 3/1992 | Forte | 623/22 |
| 5,263,988 | 11/1993 | Huebner | 623/22 |
| 5,370,702 | 12/1994 | Jones | 623/22 |
| 5,376,122 | 12/1994 | Pappas et al. | 623/22 |

FOREIGN PATENT DOCUMENTS

| | | | |
|---|---|---|---|
| 0123514 | 10/1984 | European Pat. Off. | 623/22 |
| 0277511 | 8/1988 | European Pat. Off. | 623/22 |
| 2242065 | 3/1975 | France | 623/22 |
| 8602261 | 4/1986 | WIPO | 623/22 |

Primary Examiner—Debra S. Brittingham
Attorney, Agent, or Firm—Felfe & Lynch

[57] ABSTRACT

Disclosed is a hip-joint socket for insertion into bone tissue. The hip-joint socket has an outer metal shell and an inner antifriction shell, the contact surface of the antifriction shell in the metal shell being conical in shape. The antifriction liner lies upon the conical contact surface without self-locking and the antifriction liner is fixed in the metal shell by a retaining ring. The antifriction shell is thus protected against canting and drop-out but can be removed out of its seat nondestructively and replaced.

8 Claims, 2 Drawing Sheets

TAPERED HIP-JOINT SOCKET WITHOUT TAPER LOCK

This application is a continuation of application Ser. No. 08/344,348, filed Nov. 22, 1994, now abandoned.

BACKGROUND OF THE INVENTION

The invention relates to a hip-joint socket for insertion into bone tissue, the socket being formed with an outer metal shell and an inner antifriction shell with a contact surface having a conical configuration.

Hip-joint endoprostheses consist of a hip-joint socket which is anchored in the pelvic bone and of a ball which is inserted for rotation in the socket and anchored with a shank in the thigh bone.

Hip-joint sockets consist of an outer metal shell which constitutes the external contour of the implant and is made from an internal antifriction lining made from ceramic or from plastic, i.e. Ultra High Molecular Weight Polyethylene (UHMWPE).

The term, "metal shell," is synonymous with the metal outer part of the implant anchored in the pelvic bone. The external contour is shaped in accordance with the medical requirements.

It is state of the art to affix the inner antifriction lining by means of a taper lock. The angle of the taper lock is 5°43', i.e., an angle ratio of 1:10. The antifriction liner is thus self-locked or friction-locked into the metal shell. No other fastening means are provided.

A disadvantage of this is that the antifriction liner can easily become canted when it is inserted into the metal shell. The result is an uneven distribution of forces which under certain circumstances can result in fracture of the liner, especially when the liner is constructed from a ceramic material.

Another important disadvantage is that after the insertion of the liner and socket insert, the liner can no longer be nondestructively removed on account of the high seizing forces. However, removeability is extremely important for the operating surgeon.

Another disadvantage is that, with a taper lock of 1:10, the convexly shaped portion of the antifriction liner is subjected to high tensile stresses, the result being that the liner must be made with great wall thicknesses. From the medical viewpoint, however, there is a demand for small implants.

The above discussed problems are solved by a hip-joint socket according to the invention.

The various features of novelty which characterize the invention are pointed out with particularity in the claims annexed to and forming a part of this specification. For a better understanding of the invention, its operating advantages and specific objects obtained by its use, reference should be made to the accompanying drawings and descriptive matter in which there is illustrated and described a preferred embodiment of the invention.

THE INVENTION

Figure 1:
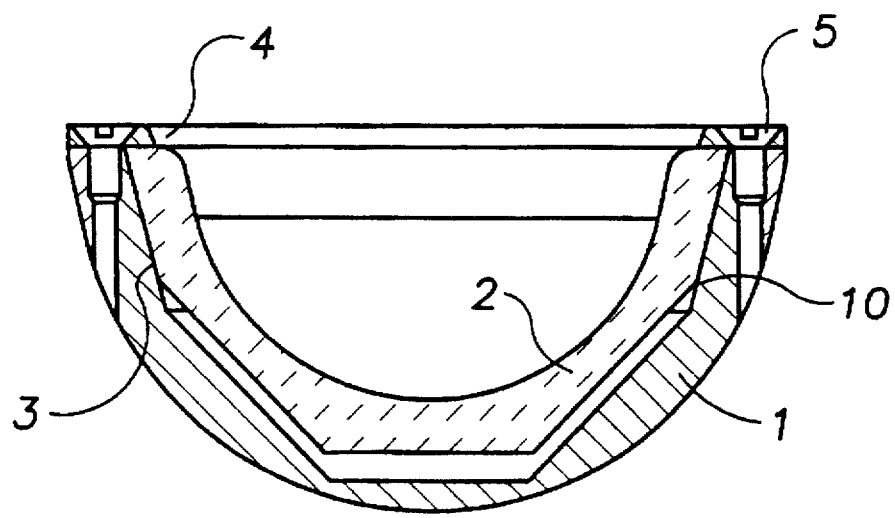
FIG. 1 is a front cut-away view of a hip-joint socket of the invention in one embodiment.

The present invention is in an improved hip-joint socket for insertion into bone tissue such that the socket insert and liner will be protected against canting and separation. In the invention, the liner can be removed from its seat, preferably by pressing, without destruction and replaced while simultaneously achieving less stress on the liner.

In the invention, the antifriction shell is in contact with the conical contact surface of the metal shell without self locking and is fixed therein by a retaining ring. Since the antifriction liner lies on the tapering bearing surface without self-locking, it can easily be removed and replaced. This is extremely important for the surgeon.

The phrase "without self-locking" means that the antifriction liner is not gripped on its seat but merely rests thereon. The antifriction liner is anchored in the metal shell by a retaining ring which alone provides the fixation of the liner.

In accordance with the invention, the angle $\alpha$ of the tapered bearing surface is between 20° and 90°, and, in a preferred embodiment, $\alpha$ is about 40°.

The retaining ring is expediently fastened to the edge of the metal shell preferably by means of screws and extends past the inner edge of the metal shell. The latter portion of the retaining ring extending past the inside edge serves as a bearing surface for the liner.

In a preferred embodiment the antifriction liner is of a ceramic material.

In an alternative preferred embodiment, the upper outside edge of the antifriction liner slopes conically inward. The liner in that case is anchored in the metal shell by a retaining ring in contact with this inwardly sloping edge. In this embodiment, therefore, the locking ring is configured as a retaining ring.

By these measures a high mechanical strength is achieved since the bearing surface is oriented in the direction of the principal stress. In this manner tensile strains are prevented and, since the liner advantageously consists of ceramic and thus has an extraordinarily high compressive strength, the implant can be fashioned with a thinner wall and low structural height.

Expediently, the upper edge surface of the metal shell, the retaining ring and the metal shell are at the same level or height. This provides the hip-joint socket with a compact structure.

In a preferred embodiment the retaining ring is screwed into, and held in the metal shell by a screw thread. In another advantageous embodiment, the retaining ring has bores and is affixed to the metal shell by screws. Each of these embodiments permits a gap-free mounting of the conical contact surfaces of the antifriction liner in the metal shell. Furthermore, the edge of the liner is compressively stressed by the retaining ring, which also has a beneficial effect on the mechanical strength of the implant.

In accordance with the invention, the sloping contact surface of the liner advantageously extends from the retaining ring or holding ring approximately to the bottom of the metal shell.

Referring to the drawings, FIG. 1 shows a hip-joint socket according to the invention. The hip-joint socket is formed of an outer metal shell 1 and an inner antifriction liner 2 which is preferably made of ceramic. The metal shell is made of a suitable material such as titanium. Metal shell 1 forms the external shape of the implant and is inserted into the bone tissue. The upper edges of the metal shell 1 and liner 2 are at the same level.

The interior of the metal shell 1 is provided with a conical bearing surface 10 for the liner 2. The bearing surface 10 extends all around the circumferential surface of the metal shell 1. The antifriction liner 2 has a bearing surface 3 that mates with that of the metal shell.

According to the invention, the antifriction liner 2 lies upon the conical bearing surface 10 without taper lock. The angle of the conical bearing surface must therefore be made large enough to avoid any seizing or taper lock. This can be achieved in the invention with any angle from 20° to 90°. Preferred is an angle α of around 40°.

Figure 2:
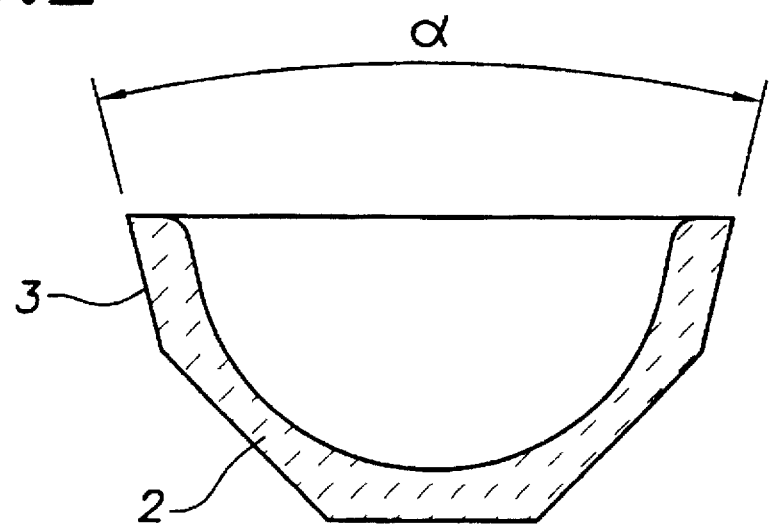
FIG. 2 is a cross-sectioned view of the antifriction liner of the type shown in FIG. 1.

FIG. 2 is a cross section of an antifriction liner 2 with the same dimensions as in FIG. 1. The taper of the contact surface 3 with the angle a is clearly depicted in FIG. 2.

FIG. 1 shows an embodiment wherein the antifriction liner 2 is anchored in the metal shell by a retaining ring 4. The retaining ring 4 is fastened on the edge of the metal shell 1 by screws 5 and extends beyond the inside edge of the metal shell 1. This area serves as the contact surface for the upper margin of the liner 2.

The hip-joint socket in accordance with the invention assures the easy removal of the antifriction liner 2 as well as its secure anchoring in the metal shell 1.

Figure 3:
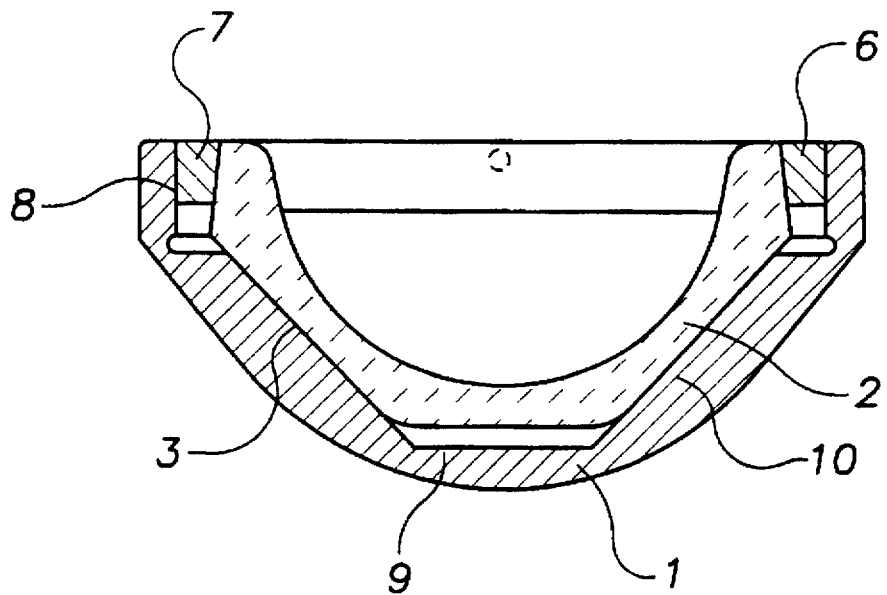
FIG. 3 shows an alternate embodiment of the invention.

FIG. 3 shows an embodiment of a hip-joint socket, also with a metal shell 1 of titanium and an antifriction liner 2 of ceramic, e.g., aluminum oxide or one of its alloys. In this embodiment, the upper external edge of the antifriction liner 2 is provided with an inwardly facing conical inclination 6. Conical inclination 6 adjoins the conical bearing surface 3 but slopes away from or opposite to the inclination of bearing surface 3. The liner 2 is anchored by a locking ring 7 as a holding ring, which lies against the conical inclination 6 and presses the antifriction liner 2 against the metal shell 1.

The edges of the metal shell 1, locking ring 7 and liner 2 are at the same level. On the outer circumferential surface of the locking ring 7 the latter and the adjacent metal shell 1 are provided with a screw threading 8 which is preferably a free thread. The locking ring 7 can thus be screwed in easily and thus presses the antifriction liner 2 against the metal shell 1. Indentations can be provided on the retaining ring surface for engagement by a tool to facilitate installation and fastening of the retaining ring.

Figure 4:
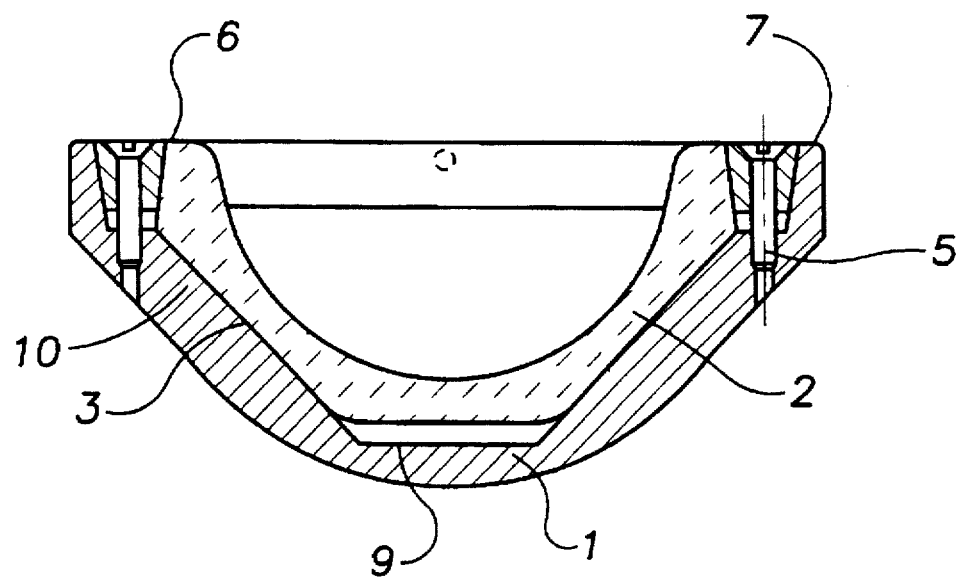
FIG. 4 shows another alternative embodiment of the invention.

FIG. 4 shows an embodiment very similar to that of FIG. 3. In this case, however, the locking ring 7 has bores through which the locking ring 7 is fastened to the metal shell 1 by screws 5. Otherwise, this embodiment is identical with that of FIG. 3. The same reference numbers also indicate the same objects.

Common to the embodiments illustrated in FIGS. 3 and 4 is that the tapering bearing surface 3 of the antifriction liner 2 extends approximately to the bottom 9 of the metal shell 1. This feature can also be provided advantageously in the embodiments represented in FIGS. 1 and 2.

It will be understood that the specification and examples are illustrative but not limitative of the present invention and that other embodiments within the spirit and scope of the invention will suggest themselves to those skilled in the art.

We claim:

1. A hip-joint socket for insertion into bone tissue comprising:

an outer metal shell having a conical bearing surface where the outer metal shell has a face and an inner edge; and a removable inner antifriction liner of a ceramic material having a contact surface with a conical configuration wherein the antifriction liner lies upon the bearing surface without self-locking and is fixed in the metal shell by a retaining ring, where the retaining ring is fastened by screws on the face of the metal shell and the retaining ring extends beyond the inner edge of the metal shell.

2. The hip-joint socket of claim 1 wherein the conical contact surface has an angle (α) and α is between 20° and 90°.

3. The hip-joint socket of claim 1 wherein the angle (α) of the conical contact surface is about 40°.

4. A hip-joint socket for insertion into bone tissue comprising:

an outer metal shell having a conical bearing surface; and a removable inner antifriction liner of a ceramic material having a contact surface with a conical configuration wherein the antifriction liner lies upon the bearing surface without self-locking and is fixed in the metal shell by a retaining ring, where the antifriction liner has an upper outer edge with an inwardly directed conical inclination which slopes away from the inclination of the contact surface and the antifriction liner is anchored in the metal shell by a retaining ring which lies against the inwardly directed conical inclination and presses the antifriction liner against the metal shell.

5. The hip-joint socket of claim 4 wherein the metal shell, the antifriction liner and the retaining ring each have an upper face and the upper face of the metal shell, of the retaining ring, and of the antifriction liner are at the same level.

6. The hip-joint socket of claim 4 wherein the retaining ring is provided in the metal shell by means of a screw thread in the metal shell.

7. The hip-joint socket of claim 4 wherein the retaining ring has holes and is fastened by screws into the outer metal shell.

8. The hip-joint socket of claim 4 wherein the conical contact surface of the antifriction liner reaches approximately to the bottom of the metal shell.

* * * * *

UNITED STATES PATENT AND TRADEMARK OFFICE
CERTIFICATE OF CORRECTION

PATENT NO : 5,725,589
DATED : March 10, 1998
INVENTOR(S): Hans-Georg Pfaff, Ernst Hoch and Harmut Kalberer It is certified that error appears in the above-identified patent and that said Letters Patent is hereby corrected as shown below:

Title page, item [73] Assignee, delete "Cera GmbH Innovatives-Keramik-Engineering" and insert therefor --Cerasiv GmbH Innovatives Keramik-Engineering--.

Signed and Sealed this

Sixth Day of June, 2000

Attest:

Q. TODD DICKINSON

*Attesting Officer*         *Director of Patents and Trademarks*